US012360037B2

(12) United States Patent
Hegarty et al.

(10) Patent No.: US 12,360,037 B2
(45) Date of Patent: Jul. 15, 2025

(54) IR SPECTROSCOPE CELL CULTURE ANALYSIS

(71) Applicant: DXCOVER LIMITED, Glasgow (GB)

(72) Inventors: Mark Hegarty, Glasgow (GB); Matthew J. Baker, Glasgow (GB); Holly Butler, Glasgow (GB)

(73) Assignee: DXCOVER LIMITED, Glasgow (GB)

( * ) Notice: Subject to any disclaimer, the term of this patent is extended or adjusted under 35 U.S.C. 154(b) by 38 days.

(21) Appl. No.: 17/792,921

(22) PCT Filed: Jan. 15, 2021

(86) PCT No.: PCT/EP2021/050849
§ 371 (c)(1),
(2) Date: Jul. 14, 2022

(87) PCT Pub. No.: WO2021/144443
PCT Pub. Date: Jul. 22, 2021

(65) Prior Publication Data
US 2023/0068250 A1    Mar. 2, 2023

(30) Foreign Application Priority Data

Jan. 16, 2020    (GB) ..................... 2000670

(51) Int. Cl.
*G01N 21/3563* (2014.01)
*C12M 1/26* (2006.01)
(Continued)

(52) U.S. Cl.
CPC ......... *G01N 21/3563* (2013.01); *C12M 33/04* (2013.01); *C12M 41/46* (2013.01); *G01N 21/3577* (2013.01); *G01N 2021/3595* (2013.01)

(58) Field of Classification Search
CPC .......... G01N 21/3563; G01N 21/3577; G01N 2021/3595; G01N 21/552;
(Continued)

(56) References Cited

U.S. PATENT DOCUMENTS 5,945,674 A    8/1999    Dukor ...................... 250/339.11
5,976,885 A    11/1999    Cohenford et al. ............ 436/63
(Continued)

FOREIGN PATENT DOCUMENTS

EP    1489162    12/2004
EP    1489162 A2 *  12/2004    ......... G01N 21/3563
(Continued)

OTHER PUBLICATIONS

Fale et al., In situ Fourier transform infrared analysis of live cells' response to doxorubicin, Jul. 29, 2015, Biochimica et Biophysica Acta vol. 1853, pp. 2640-2648. (Year: 2015).*
(Continued)

*Primary Examiner* — David P Porta
*Assistant Examiner* — Fani Polyzos Boosalis
(74) *Attorney, Agent, or Firm* — Medlen & Carroll, LLP

(57) ABSTRACT

A method of detection of a status of cells within a cell culture is described. The method is based on comparing an IR spectrum of a test sample obtained from the cell culture with an IR spectrum of a control sample or samples or with an IR spectrum of a sample or samples obtained at an earlier time point in the cell culture and correlating differences between the spectra with the status of the cells. The status may be classified into healthy or unhealthy. The test sample may or may not contain cells. The test sample may contain cell fragments, cell components or cell media, or may be cell supernatant. The comparison may be performed using a predictive model based on pattern recognition algorithms, such as support vector machines SVM, linear discriminant
(Continued)

analysis LDA, principal component discriminant function analysis PC-DFA, neural networks, or random forests). The analysis results may be used to monitor and/or control the cell culturing process.

14 Claims, 18 Drawing Sheets

(51) Int. Cl.
  *C12M 1/34* (2006.01)
  *G01N 21/3577* (2014.01)
  *G01N 21/35* (2014.01)
(58) Field of Classification Search
  CPC ... G01N 2021/8416; G01N 2201/1293; C12M 33/04; C12M 41/46
  See application file for complete search history.

(56) References Cited

U.S. PATENT DOCUMENTS

| | | |
|---|---|---|
| 2011/0024630 A1 | 2/2011 | Sundaram |
| 2011/0236922 A1 | 9/2011 | Burns |
| 2015/0301017 A1 | 10/2015 | Baker et al. |
| 2017/0167976 A1 | 6/2017 | Wood et al. |
| 2019/0272894 A1 | 9/2019 | Wasalathanthri |
| 2019/0369015 A1 | 12/2019 | Ismail |

FOREIGN PATENT DOCUMENTS

| | | |
|---|---|---|
| EP | 2299259 A1 | 3/2011 |
| WO | WO/2005/020125 | 3/2005 |
| WO | WO/2012/178157 | 12/2012 |
| WO | WO/2013/175312 | 11/2013 |
| WO | WO 2014076480 | 5/2014 |
| WO | WO2015/085056 | 6/2015 |
| WO | WO/2016/102056 | 6/2016 |
| WO | WO2018/178669 | 10/2018 |

OTHER PUBLICATIONS

Sampaio et al ("High-throughput FTIR-based bioprocess analysis of recombinant cyprosin production"), J Ind Microbiol Biotechnol (2017) pp. 49-61. (Year: 2017).*
Search Report issued for the UK priority application (GB 2000670.6) dated Apr. 15, 2020.
International Search Report and Written Opinion mailed on Apr. 21, 2021.
International Preliminary Report on Patentability PCT/EP2021/050849, dated Jul. 28, 2022.
Hashimoto, A. et al. (2014) "Infrared Spectroscopic Analysis on Kinetic Sugar Uptake Phenomena of Suspension Plant Cells(<Feature>Control and Diagnosis by Light in Plant Production)," Journal of the Illuminating Engineering Institute of Japan 98(9), 512-515.
JP Notice of Reasons of Refusal mailed Jun. 25, 2024 for JP 2018534587 (=WO 2017042579 A1) for Foreman et al. (English translation also included).
European Patent Office Action for the European Patent Application No. 21701424.0 dated Mar. 21, 2024.
Japanese Patent Office Action for the Japanese Patent Application No. 2022-543587 dated Mar. 19, 2024.

* cited by examiner

IR SPECTROSCOPE CELL CULTURE ANALYSIS

FIELD OF THE INVENTION

The present invention relates to methods for performing infrared spectroscopy (IR) analysis on cell cultures, in order to detect any potential abnormalities in cells, which are present in the cell culture.

BACKGROUND OF THE INVENTION

Fourier Transform Infrared (FTIR) spectroscopy is a technique commonly used in chemical sciences in order to identify discrete vibrations of chemical bonds. This technique uses light generally in the mid-infrared (MIR) region (4000-400 $cm^{-1}$) that is, in the same frequency range as the frequency range of specific chemical bond vibrations.

Biological molecules are known to actively vibrate in this range of wavelengths, and thus FTIR spectroscopy lends itself to biological applications. When a biological sample is irradiated with MIR light, some of this energy is absorbed by the sample. The absorption profile of a given sample is representative of the chemical bonds present within a sample, and can be used to characterise complex biological materials.

An example of a particular type of analysis using FTIR spectroscopy is in the investigation of proliferative disorders, such as cancer, which are caused by uncontrolled and unregulated cellular proliferation and can, in some cases, lead to the formation of a tumour.

Recently a method of diagnosing brain cancer by performing Attenuated Total Reflection-Fourier Transform Infrared (ATR-FTIR) spectroscopic analysis of blood samples has been described in WO 2014/076480). In contrast to conventional ATR-IR (where a sample is placed on a substrate that is then brought into contact with the ATR crystal), the ATR crystal was used as the substrate for the sample. This method provides a point of care and non-destructive diagnostic test.

In the field of biological product manufacture using cells, known as bioprocessing, the cells are typically initially grown in small bench-scale batches, before scale-up. Scaling-up of the cell culture and cells within the culture, typically mammalian cells, is both time consuming and costly. Moreover, the biological product which is to be produced is generally of high value and so it is important that the cells which are used to produce the biological product are healthy, in order to produce the highest levels and quality of the biological product. However, the scaling-up process may be carried out over a number of weeks and/or in different increasingly sized bioreactors, before the final full-scale process and bioreactor is achieved. This scaling-up of an upstream process can result in cell abnormalities occurring, such as due to contamination causing bacterial or viral infection, or problems associated with inhibited or inefficient cell growth. The sooner such abnormalities can be detected the better, in terms of process control and cost efficiencies. Moreover, in some instances, the required biological product may only be expressed once the cell culture has been scaled-up to its maximum and in such instances, a user may not know there is any problem with the cells and hence their ability to produce the biological product, until after a great deal of time and expense has been incurred.

In view of the above, it would be desirable to be able to monitor cells within a cell-culture, typically during any stage of a bioprocess, including upstream and downstream processes, in order to be able to quickly ascertain the health of the cells within the cell culture and whether or not the scaling-up process is proceeding satisfactorily, or not.

SUMMARY OF THE INVENTION

The present teaching is based on studies made by the inventors into IR analysis of cells and/or the cell medium within a cell culture and the inventors' observations that it is possible, from the IR analyses, to detect differences, such as healthy versus unhealthy status, in cells.

Thus, in a first aspect, there is provided a method for detecting a status of cells within a cell culture, the method comprising:

providing an IR spectrum from a test sample obtained from a cell culture; and comparing the IR spectrum with an IR spectrum of a control sample or samples, or a sample or samples obtained at an earlier time point of the cell culture to the test sample, in order to detect any difference between the test and control or earlier samples, which can be correlated with the status of cells within the test sample obtained from the cell culture.

The sample or samples may be obtained from the cell culture manually, or may be obtained by a semi-automated, or fully automated system associated with the cell culture.

Thus, in a further aspect there is provided an integrated cell culture and IR analysis system comprising:
  a) cell culture apparatus for growing cells in culture;
  b) a sample handling system for obtaining one or more samples from a cell culture within the cell culture apparatus, the sample handling system comprising a sampler for obtaining a sample from the cell culture and transporting the sample to an IR spectrometer in order that an IR spectrum of the sample or samples may be obtained; and
  c) conducting the method according to the first aspect, or embodiments thereof, so as to detect the status of cells within the cell culture.

The method according to the first or further aspect may generally include a computer system with integrated software in order to conduct the comparison step and detect any differences between the test sample and control or earlier samples obtained from the cell culture. Such a computer system will typically include a display device in order to provide a user with a result of the comparison.

The "status" of cells within the cell culture, may relate to, for example, the health of the cells. That is, whether or not the cells within the cell culture are considered to be healthy, or unhealthy. Unhealthy cells may be diseased, such as due to infection by a virus or bacteria, for example, or may have developed an abnormality due to the cell culture conditions and/or a mutation occurring in the cells. An abnormality occurring due to cell culture conditions may arise due to, for example, a change in pH, oxygen levels, nutrient levels, and the like. Essentially, any less than optimum conditions may result in changes occurring in the cells in the cell culture and a change in the status of the cells within the cell culture, which may then impact on the quality and/or yield of bioprocessing product downstream.

In the integrated system of the further aspect, the integrated system may further comprise the ability to alter and/or halt the cell culturing process in response to any result(s) obtained from the method. Thus, for example, if the method detects that the cell culture may include cells which are considered to be nutrient deficient, the system may alter one or more nutrients which are being provided to the cell culture, or alert the user to conduct a more thorough process, such as a necessary passage step. Further analysis (i.e. running the method again following nutrient alteration) may determine whether or not the nutrient alteration has been sufficient in addressing the cell status. Additionally or alternatively, the integrated system may have the ability to shut down the cell culture when, for example, an infection is detected. The ability to be able to adapt and/or shut down a cell culture quickly may provide real efficiencies and/or cost savings to a user.

The cell culture may be any suitable in vitro cell culture in which cells are grown in vitro, typically in order that the cells produce a product, such as a recombinant protein or the like. However, the cells themselves may be the product, such as when the cells may be used as a vaccine or as a therapeutic product themselves, such as in cell therapy applications known in the art. Additionally, cells may find application in in vitro applications, for example in drug testing, or in research applications and it is important to ensure the quality of such cells, regardless of their end-use. The cells may be bacterial or eukaryotic, such as mammalian or other eukaryotic cell types.

The IR spectrum which is provided, is typically an FTIR spectrum, or a portion or portions thereof. As will be further described herein, the IR spectrum, such as FITR spectrum, or a portion or portions thereof, may be subjected to further spectral processing, as known in the art, in order to carry out baseline correction and/or normalisation and reduce, for example, unwanted variance from the dataset, which may arise due to optical pathlength differences, instrument, instrumental and environmental factors, as well as noise and general variance. Prior to a spectroscopic analysis, a background spectrum may be obtained. Such background spectra may provide correction for a background environment, such as air or the culture medium in which the cells are grown. Thus, the IR spectrum, or a portion or portions thereof, may be an IR spectrum which has been subjected to such background correction. Additionally, or alternatively, the IR spectrum, or a portion or portions thereof, can be subjected to further processing of the measured IR spectrum or a portion or portions thereof, for example using multivariate analysis (such as Principal Component Analysis (PCA)), processing algorithms, and/or machine learning. For example, the use of PCA allows variance between datasets to be compared, visualised and/or explored, thus identifying possible variations, e.g. biological variations, between samples.

There are three principal sampling modes used in FTIR spectroscopy: transmission, transflection, and attenuated total reflection (ATR), one or more of which may be used in accordance with the present invention.

In the "transmission" mode, MIR light is passed, or transmitted, directly through a given sample that has been deposited on an IR transparent substrate (such as $CaF_2$ or $BaF_2$). As this mode is reliant upon the IR beam passing through the sample, there are constraints to maximum sample thickness and water content.

In the "transflection" mode, a sample is deposited on an IR reflective slide (such as low-E or metal coated). MIR light is passed through the sample and it is then reflected back towards the detector. As the beam is effectively passed through the sample twice, the sample thickness has a direct effect on path length and therefore signal strength. This also allows further absorption of water, if at all present in the sample. There are some known concerns in the field regarding this form of sampling due to undetermined interaction of light with the reflective surface of the substrates.

"Attenuated Total Reflection" (ATR) employs an internal reflective element (IRE) through which the IR beam is passed. The sample is deposited directly onto the IRE, and maintained in close contact with it. These IREs can be made from a number of different materials, including diamond, germanium, zinc selenide or silicon. Each material differs slightly in its refractive properties. When IR light is passed through an IRE above a defined angle, described as the critical angle, the light is internally reflected through this medium. When the beam meets the IRE and sample interface, this results in the production of an evanescent wave which penetrates into the sample. The depth of this penetration is dependent upon the wavelength of light, the refractive indices of the IRE and the sample, as well as the angle of incidence: however, is generally in the region between 0.5-2 μm. The beam is then reflected by the IRE towards a detector.

One benefit of ATR-FTIR spectroscopy is the reduced influence of water absorbance on the IR spectrum, allowing the interrogation of water-containing samples. This is particularly important to cells and cell culture samples which will intrinsically contain water. Although water molecules still absorb in this sampling mode, the penetration depth of the evanescent wave is much smaller than the path length of transmission and transflection FTIR spectroscopy. Therefore, much less water is being sampled, allowing the underlying sample absorbance to still be monitored.

WO2018/178669, the entire contents of which are hereby incorporated by way of reference, describes suitable methods and devices for use in accordance with the present invention and the skilled reader is directed to this teaching.

Any number of scans may be employed, but typically the FTIR spectroscopic analysis employs at most 100 scans, suitably at most 50 scans, and most suitably at most 40 scans, such as between 8-32 scans. Suitably the scans are co-added. The number of scans is suitably selected to optimize data content and data-acquisition time.

Suitably IR spectra are collected to include the region of 400-4000 wavenumbers (cm'). The IR spectra may have a resolution of 10 cm-1 or less, suitably 6, 5, 4 cm-1 or less. The spectroscopic signature characteristic of the sample (i.e. signature region) is suitably part or all of the relevant IR spectrum between 500 to 2500 cm-1, more suitably part of all of the spectrum between 800 and 2000 cm-1, and most suitably the spectrum between 900 and 1800 cm-1.

The spectroscopic analysis may involve vector normalisation as a pre-processing step.

As mentioned above, the present invention is directed to methods for detecting a status of cells within a cell culture. The methods may be carried out on samples obtained from cell culture, such samples may be liquid samples, which are analysed in a wet or dry state. A dry state may be obtained from a wet sample which has been allowed to dry. As used herein, a "wet" sample refers to a sample which has not been dried prior to spectroscopic analysis. As such, the sample may contain water (e.g. up to 95% water) and/or be in liquid form. A sample may or may not comprise cells from the cell culture. In one embodiment, the sample comprises cells from the cell culture. If the sample does not comprise cells, the sample may comprise cell components, or cell fragments, which have been released into the cell culture medium.

Alternatively, the method may comprise monitoring non-cellular material within the cell media, for example, in order to detect any changes in nutrient levels and/or to identify the presence of any infectious agents. Such methods may provide an indirect method of detecting cell status within the cell culture, whereby detecting any change in the non-cellular material may be correlated with cell status. Additionally, the end-product, sometimes referred as the downstream product, may be monitored, as this may also give an indication of the cell status. Where the product is a recombinant protein, for example, which is produced by cells in the cell culture, any changes in production of the protein may be detected in accordance with the invention. Any changes, such as a reduction in protein production, may indicate that the cells are not healthy and/or not present in optimum culture conditions. This would allow a user or automated system the opportunity to address this.

As observed by the inventors, the sample may be a sample, which has been obtained and stored, for example, by freezing the sample and thawing and/or fixing the sample before analysis. Such freeze/thawed and/or fixed samples can still be analysed in accordance with the present invention and provide suitable spectral information.

The method may comprise taking a single sample from the cell culture, or a series of samples, taken at various points during the cell culture and/or scale-up process. A negative, or control sample, may comprise a sample of cell culture medium without cells or cell fragments present, or a control sample, which is of known cell status. For example, such a control sample may include cells, which are known to be healthy or indeed infected or nutrient deprived. A user will then be able to compare a test sample, with the control sample in order to identify if the test sample displays any differences in cell or cell culture status.

As mentioned previously, as an alternative to comparing the test sample spectrum with a control sample spectrum, it is also possible to compare a test sample spectrum with sample spectrums, which have been obtained from earlier in a cell culture process. By comparing spectra from two separate time points, a user can observe whether or not any changes have occurred over time, which would indicate a change in cell or cell culture status.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

A sample may be suitably centrifuged or filtered to separate cells and/or cellular material from bulk liquid of the sample. Centrifugation, as appreciated by the skilled reader, will be relatively gentle in order to achieve suitable pelleting of cells and/or cellular material, without causing substantial damage or lysis of the cells or cellular material. As an example, centrifugation at 1000 rpm for 1 minute or less may be sufficient. Filtering of cell culture samples suitably involves, for example, filtering through a filter in order to separate cells and/or cellular material from the culture medium and any soluble material therein. A user can choose a suitable filter depending on the circumstances and the cells which are being cultured.

Comparing the IR spectra/the analytical results may be performed manually (e.g. by a cell culture technician or other suitable analyst) or automatically (e.g. by computational means). Comparisons may be established qualitatively (e.g. via a comparison of graphical traces or signatures) or quantitatively (e.g. by reference to predetermined threshold values or statistical limits). 'Comparing the analytical results may be performed using a predictive model, optionally as defined herein, which may have been developed by "training" a database of pre-correlated analyses.

In a particular embodiment, comparing the analytical results, so as to detect or determine the status of cells within the cell culture, involves an initial comparison of the analytical results with a reference standard or with previous analytic results that have already been correlated with a particular status (e.g. pre-correlated analytical results stored in a database). Correlations with previous analytical results may involve a statistical comparison or a "best fit" comparison (e.g. if comparing graphical traces with those stored in a database). The method of correlating the analytical results may be a computer-implemented method of correlating. Suitably such computer-implemented methods incorporate predictive models, optionally in conjunction with appropriate databases. These predictive models may be auto-generated using pre-defined database frameworks that may be populated by the end user.

Suitably, before correlating any analytical results, the analytical results are themselves validated. In particular, the analytical results should ideally be first validated as being definitive and without artefacts that can arise through variation in sample preparation and the like.

In a particular embodiment, a spectroscopically obtained IR spectrum or processed spectrum/data as described herein, is compared to a plurality of pre-correlated IR spectra/processed spectra/data stored in a database (e.g. a "training set") in order to derive a correlation with a particular cell status, such as healthy/unhealthy; infected/non-infected. Statistical analysis (e.g. via pattern recognition algorithms) may be suitably performed, preferably based on a comparison of the similarities and dissimilarities of the IR spectra or processed IR spectra/data with the pre-correlated signatures, before the statistical analysis is used to correlate the spectra/data with cell status. Suitably pattern recognition algorithms include support vector machines (SVM), linear discriminant analysis (LDA), principal component discriminant function analysis (PC-DFA), artificial neural networks, and random forests, which are commercially available and well known to the skilled reader.

In a particular embodiment, a spectroscopically obtained IR spectra, or processed IR spectra/data is correlated with cell status based on a predictive model developed by "training" (e.g. via pattern recognition algorithms) a database of pre-correlated analyses.

A predictive model can be furthermore established from the database through "training" the data. Such a model may then be incorporated into computer software for future predictive purposes. The signatures may then be all combined and separated (optionally randomly or selectively) into a "training set" of IR spectra or processed IR spectra/data and a "blind set" of IR spectra or processed IR spectra/data. The "training set" is then suitably trained using pattern recognition algorithms (e.g. using a support vector machine, such as those available through LIBSVM, or a PC-DFA), suitably by performing a grid search, for example to optimise the cost and gamma functions to ensure that it can identify a training set, to thereby produce a viable predictive model. The "blind set" may then be offered to the model, which is then asked to predict whether the individual IR spectra or processed IR spectra/data in the blind set should correlate to a particular cell status. The predictions can then be translated into a "confusion matrix" illustrating which predictions were made. These predictions can then be validated (e.g. by verifying the actual result, e.g. from a cell culture of known status) to calculate the sensitivity and specificity of the model.

The predictive model desirably has a sensitivity greater than 75%, more desirably greater than 80%, most desirably greater than 85%. The predictive model desirably has a specificity greater than 85%, desirably greater than 90%, more desirably greater than 98%.

Naturally, the model can be updated and refined as further results are obtained and correlated, and further criteria and variables are accounted for.

The model, once established, can be incorporated into suitable computer software. A computer running pursuant to the suitable computer software (and optionally also to the database) is then suitably configured by said software to perform predictive cell status analysis (suitably with the sensitivity and specificity established as above) upon newly inputted non-correlated IR spectra or processed IR spectra/data to thereby correlate said spectra/data with cell status.

As such, the present disclosure further teaches a computer installed with suitable computer software configured to operate the computer to perform a predictive cell status analysis based on a spectroscopic IR spectra or processed IR spectra/data of a cell culture sample. Suitably, the suitable computer software incorporates a predictive model derived from one or more pattern recognition algorithms applied to a plurality of pre-correlated IR spectra or processed IR spectra/data. The computer may also be installed with a database, as defined herein, to help correlate results with known cell status samples and/or to store training set data.

In a further aspect of the invention, there is taught a computer-readable medium containing suitable computer software and optional database as defined herein.

In a further teaching, there is taught a computer-implemented method of correlating the results of the spectroscopic analysis as defined herein with cell status within a cell culture, the method comprising:
 collecting data from said spectroscopic analysis; and
 employing a predictive model, suitably based on pattern recognition algorithms conducted upon pre-correlated spectroscopic analyses (optionally in conjunction with a database, as defined herein) to correlate said data with cell status of cells within the cell culture.

The present invention will now be further described by example, with reference to the following figures which show:

MATERIALS, METHODS AND RESULTS

Sample Preparation

Figure 1:
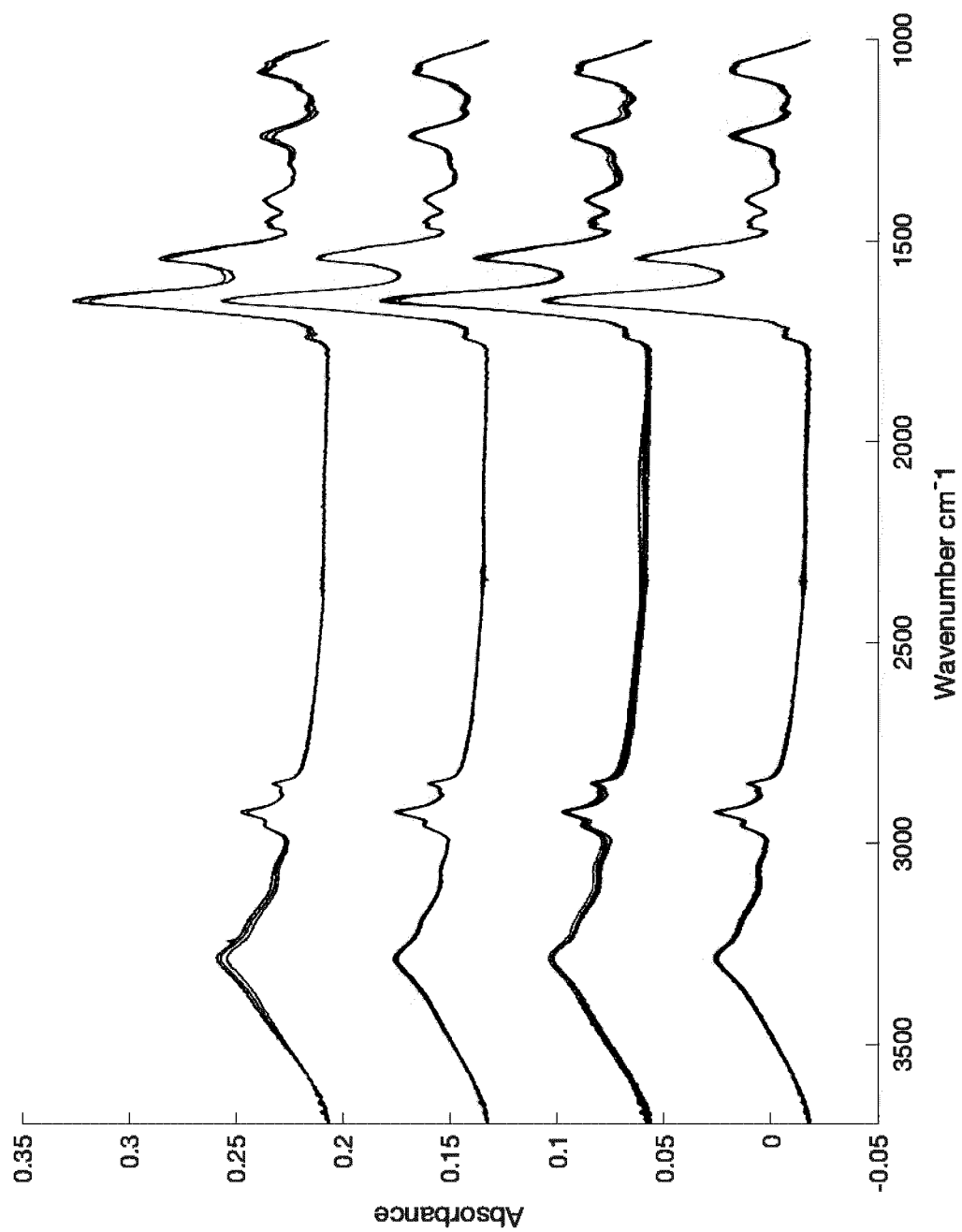
FIG. 1 shows the spectral analysis of dried CHO cells which are healthy, grown under nutrient deficient conditions or are virus infected.

It is possible to obtain a number of samples from cell culture systems, in the form of cell suspensions, or pellets, supernatant, which may or may not contain cell fragments, or as media directly from the cell culture. Sampling points could be either directly from the active culture system, or in between passage stages in the seed train process. In this instance, concentrated cell suspensions were obtained during the passage process of producing cells, where cell monolayers are removed from the culture flask using trypsin, and concentrated using centrifugation. In this state with additional cell culture media, cells can be immediately seeded into flesh culture flasks for continuous growth, or stored at −80° C. for later analysis. For this analysis, cells were analysed following freezing.

Initially cells were thawed prior to preparation for spectroscopic analysis. Cells were analysed immediately following thawing, and following cell fixation. For immediate analysis, cells were thawed in a water bath at 37° C., gently inverted, and immediately centrifuged for 3 minutes at 1000 rpm to concentrate the cells into a pellet. The supernatant was then aspirated and contained for separate analysis. Three microlitres of the cell sample was then deposited on each of the three wells of the ClinSpec Dx Optical Sample Slides. The cell sample maintained sufficient viscosity for pipetting, as some residual solution remained. For cell fixation studies, cells were also thawed in a water bath at 37° C. and gently inverted, then the thawed solution was first mixed 1:1 vol with ethanol, gently mixed with a pipette, and subsequently centrifuged at the same parameter settings; the supernatant was then discarded and only the cell pellet analysed. For all cell samples, the slides were analysed immediately after deposition to investigate the samples in a wet state, and in full following 30 minutes drying. For supernatant deposition a larger sample volume of 6 microlitres was used so that the SIRE surface was sufficiently covered.

Sample Analysis

Prior to analysis, spectra are usually pre-processed in order to remove unwanted variance from the dataset, such as sample thickness, that can mask the true biological variance within the sample. There are numerous approaches to this process, and these have been extensively checked within this study. Generally, the presented spectra are processed by baseline correction and normalisation, across the full spectrum or cut to the fingerprint region.

Generally, spectral analysis can be split into three parts; (i) spectral observation, (ii) variance exploration and (iii) classification modelling. In overview, each spectrum is first observed by eye to identify any differences in the IR spectra of the samples and try to discern any differences between the treatments, in this case, cell health. As sometimes differences cannot be observed, multivariate techniques, such as principal component analysis (PCA) permits looking at the variance alone within the dataset, which can unearth subtle differences between cells. PCA works by reducing the dimensions of the spectral dataset into principal components (PCs) that account for the variance in the data. These can be visualised as scatterplots, where spectra are single points and clustering can infer similarity, and separation between points can suggest differences. PC loadings plots can then suggest where in the spectrum this variance is arising from. Finally, classification models can be used to statistically separate the data, and to see how well the data can be accurately predicted. This can provide a level of sensitivity/specificity to analyses, similar to that of a disease prediction.

Initial results from unprocessed spectra, displayed evidence of unwanted variance in the form of baseline differences that should be minimised, in order that spectra can be directly compared. The inventors observed that baseline correction and normalisation reduced these effects so spectral differences can be more clearly seen. In this instance, a rubberband baseline correction and a subsequent vector normalisation step was applied using the mathematical software R.

FIG. 1 shows the spectral differences between healthy cells and those which have been infected by a virus and/or subjected to nutrient limitation. These samples have been analysed immediately following thawing from the frozen sample and dried onto the surface of the IRE. This nutrient depletion was induced by simply allowing the cells to grow in media for longer than recommended, in this case up to 10 days, so that nutrient levels were low. Some clear differences in the water (OH) content of the cells (3500-3000 cm$^{-1}$), and the carbohydrate region (1300-1000 cm$^{-1}$) in the fingerprint region, can be seen between healthy and 'unhealthy' cells respectively. Thus, following processing of the spectral data in order to reduce unwanted variance, spectral differences between healthy and unhealthy cell cultures can be seen. These difference however can be subtle to the user, and not always visible by eye.

Principal component analysis (PCA) can further show variance, which serves to distinguish how the different cell culture conditions effect the spectra obtained, as the different data classes begin to cluster together. This process reduces a dataset into key sources of variance, known as principal components (PCs), which encompass spectral differences. Variance can be visualised by comparing these PCs as a scatterplot, where different PCs can be plotted comparatively. Separation on a scatterplot between classes infers differences, and clustering infers similarities. Often scatterplots are presented as PC1 versus PC2, as these two components account for the most amount of variance in the dataset (PCs have descending variance values as the PC number increases, with PC1 accounting for the greatest source of variance in the dataset). The variance can be further explored as a PC loadings plot, which correlates these differences to the original IR spectrum. For example, if two classes separate visually on the PC2 axis on a scatterplot, a PC2 loadings plot will subsequently show where that variance is arising from in the IR spectrum.

Figure 2:
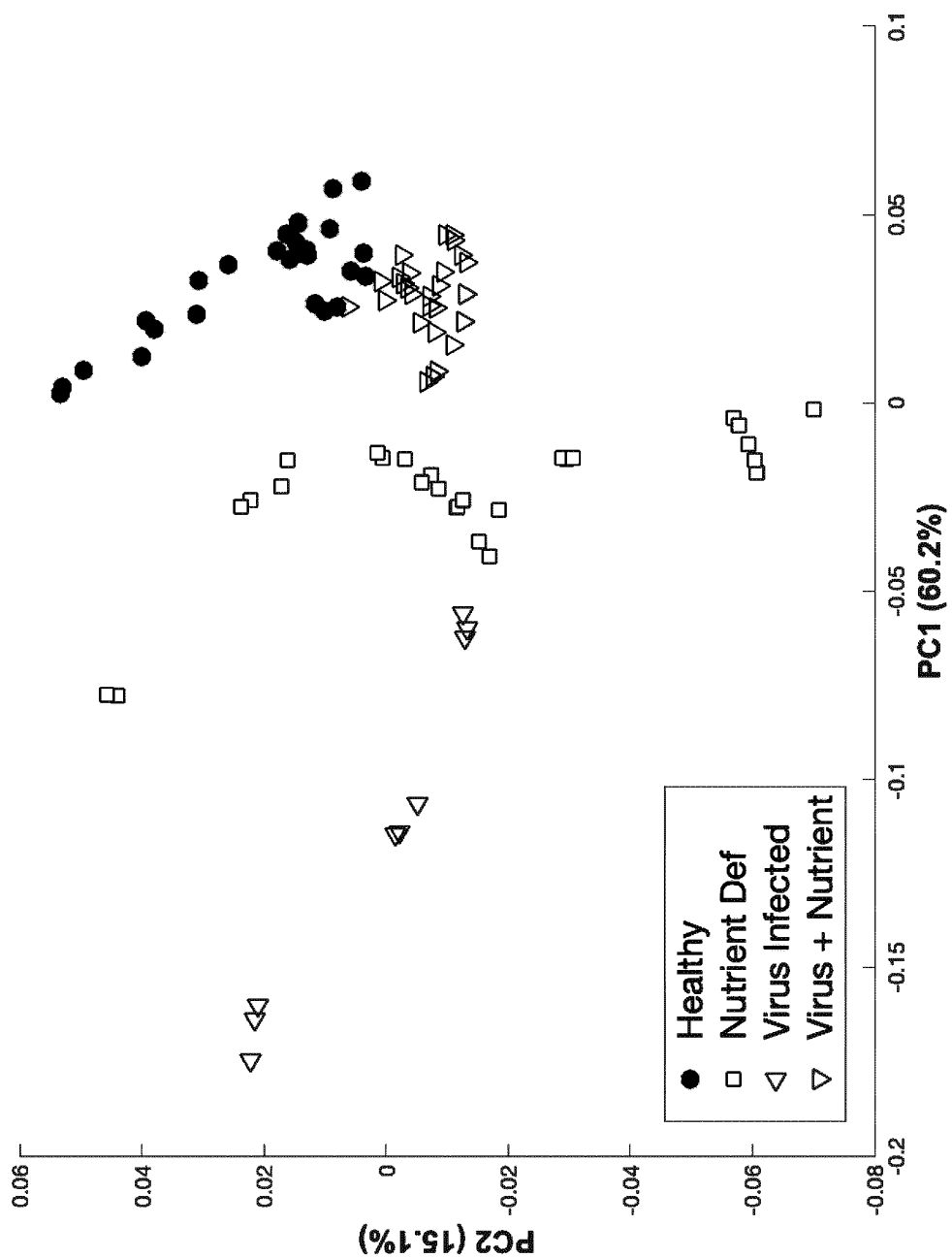
FIG. 2 shows PCA processed analysis of dried CHO cells obtained from the spectral data displayed in FIG. 1.

As shown in FIG. 2, PCA begins to differentiate the different cell statuses based on the spectral variance between them. In this example, PC1, accounting for 60% of variance in the dataset, begins to split virus infected cells, nutrient deficient from healthy and the other virally infected cells. PC2 on the other hand, begins to split healthy from virally infected cells. As the cell classes appear as distinct clusters in this PCA scatterplot, it is clear that there are biological difference that are being elucidated by spectral analysis.

Figure 3A:
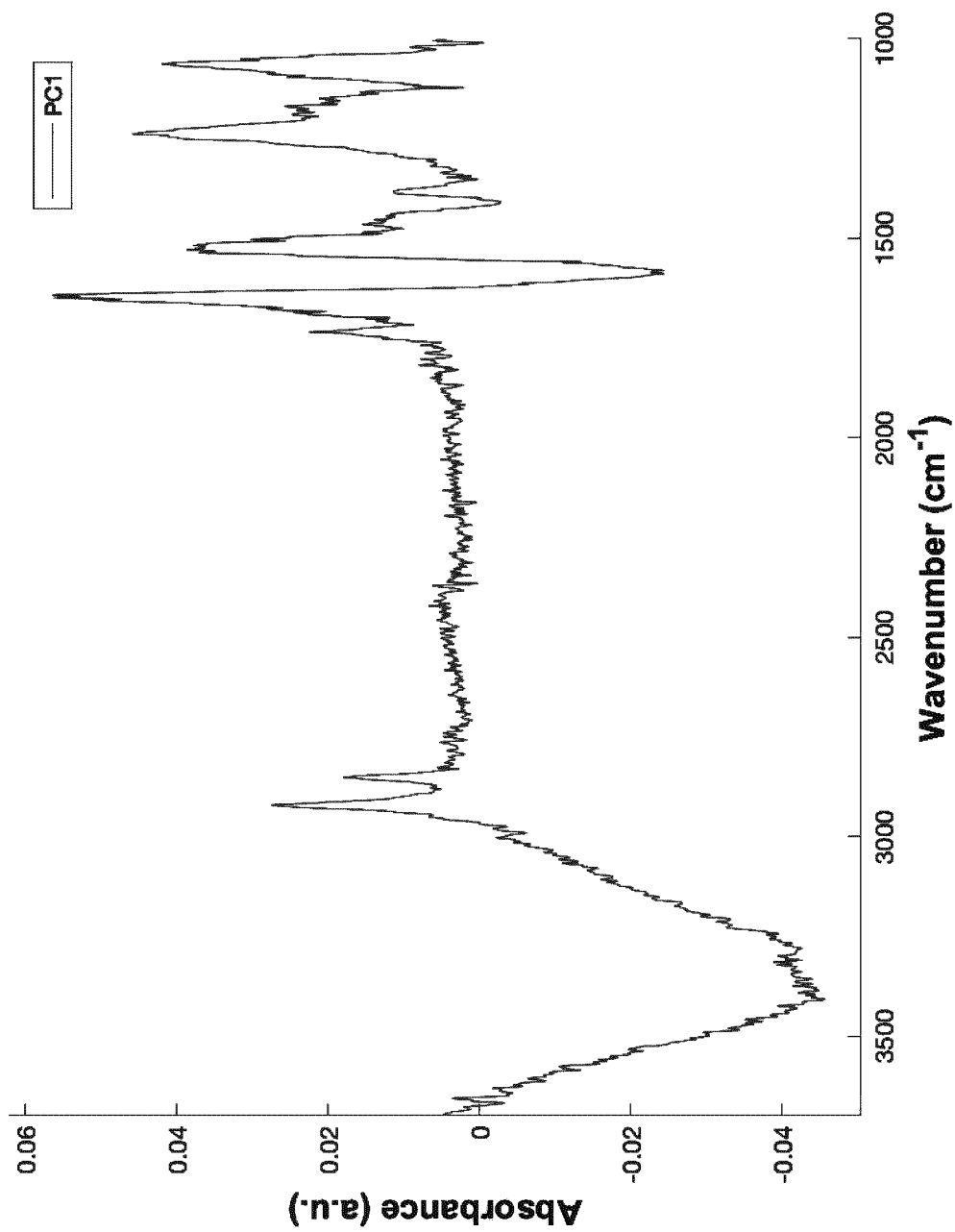
FIG. 3a shows the PC1 loadings referring to the PCA scatterplot displayed in FIG. 2.
Figure 3B:
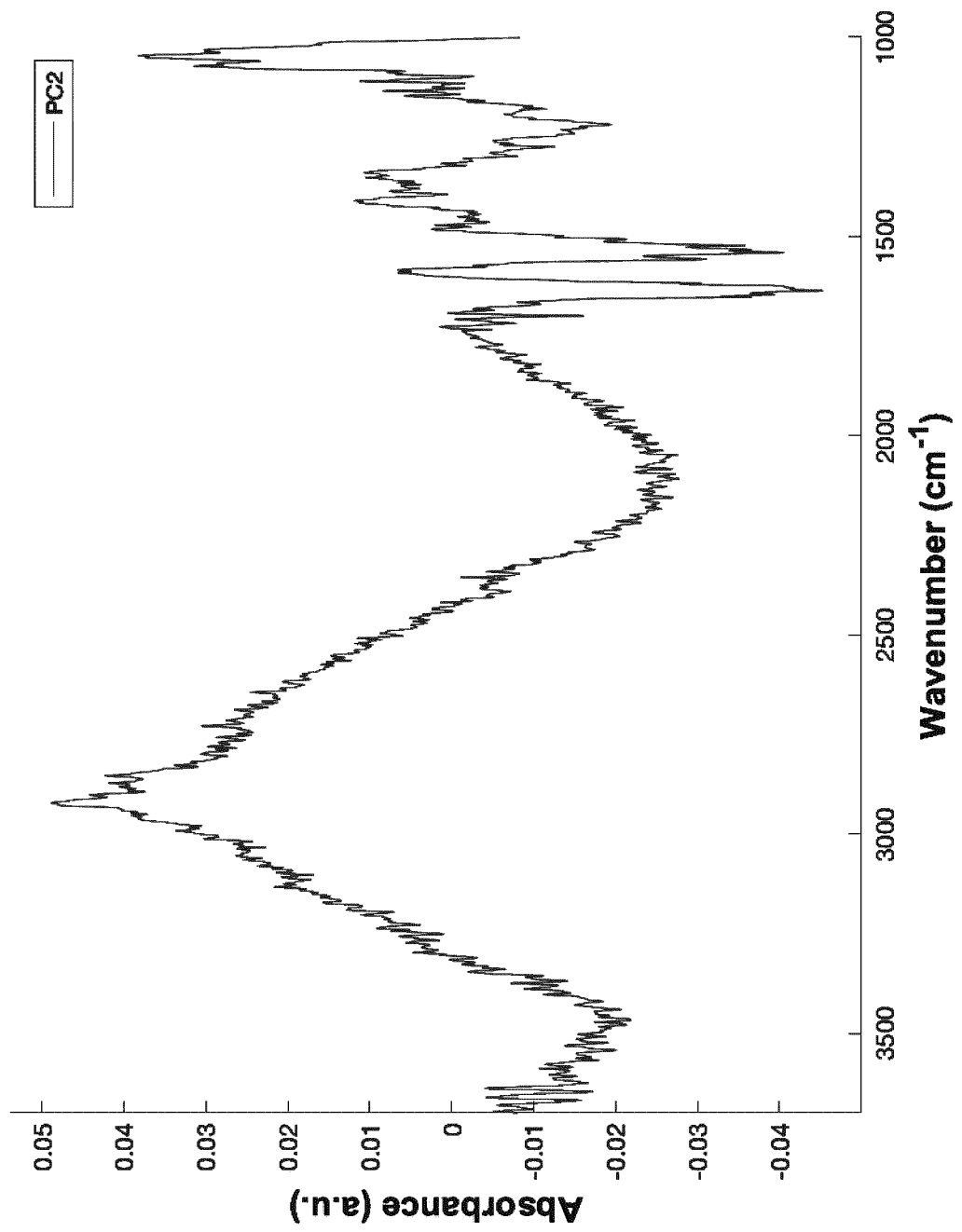
FIG. 3b shows the PC2 loadings, showing where spectral differences arise between healthy and virally infected cells.

The loadings for these PCs can show where this variance arises from in the spectrum. Negative in PC1 that differentiate the nutrient deficient and virally infected cells, appears to be associated with water (O—H) content and positive in PC1 shows more significant differences in the fingerprint region, associated with proteins and carbohydrates specifically (FIG. 3a). Positive in PC2 separates healthy cells from virally infected cells, which the loadings suggest is again a difference in the O—H stretching peak, associated with water content (see FIG. 3b). The larger amount of noise in this plot is representative of the high noise and low variance value of PC2. Whilst spectral differences were observable in FIG. 1, this analysis shows further detail and sources of these differences between healthy and abnormal cells.

Figure 4:
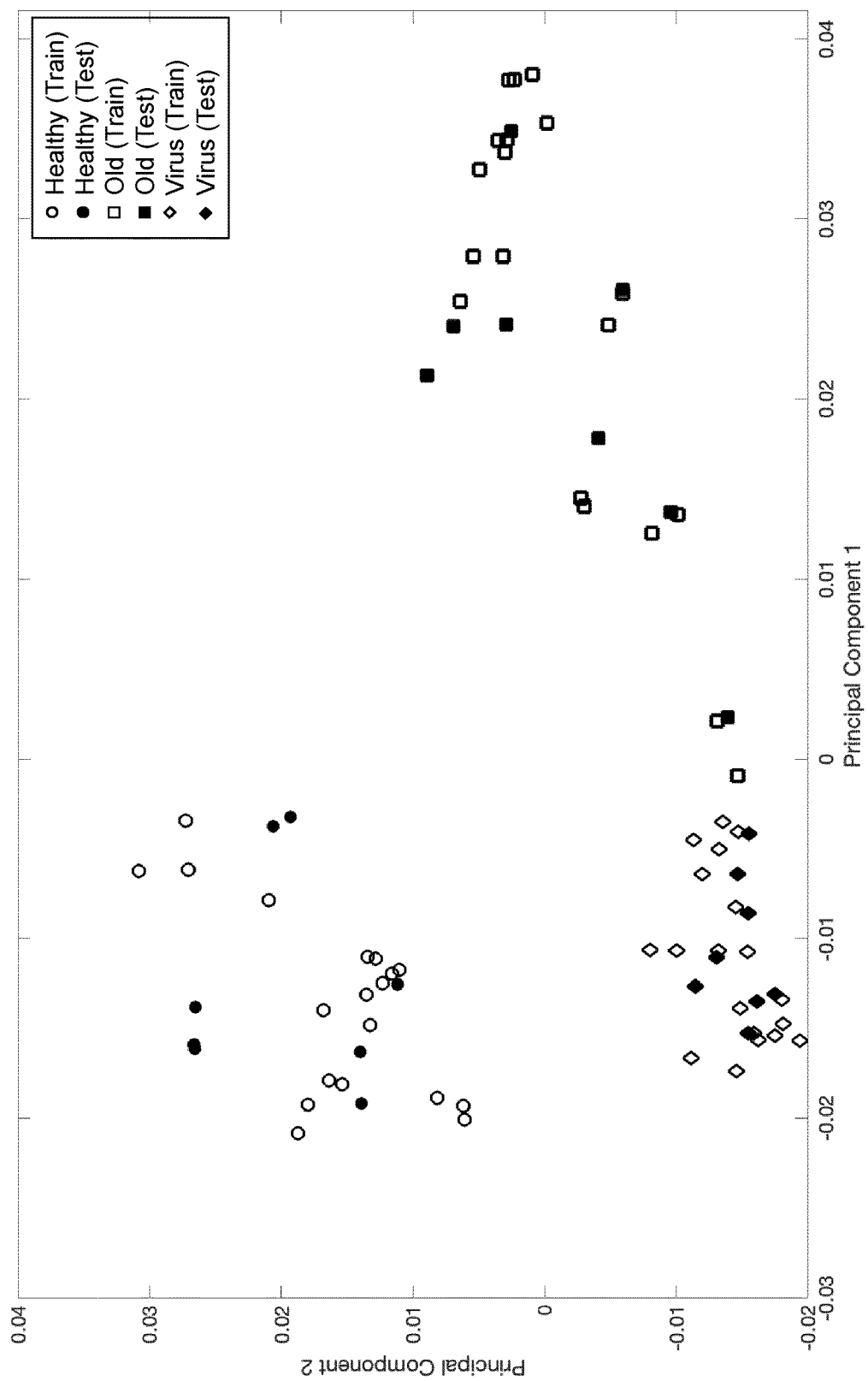
FIG. 4 shows projected PCA scatterplot analysis of healthy, virally infected and nutrient depleted ('old) samples.

Projecting these samples as a test into a PCA (see FIG. 4), shows that it is possible to correctly separate the cell types. Projected PCA, and PCA-DFA are commonly implemented analysis methods, that can be accessed in programs such as R or Matlab. Here we used the Biocluster Toolbox for Matlab. Highlighted labels are the test spectra that were projected onto the training data. Closeness represents similarity between the spectra. This process is similar to an envisaged commercial application of this technology, where unknown test samples will be compared against an existing database, with known signals of cell status, and predicted against it.

Next is the process of classification. There are a large variety of classification algorithms available, such as SVM, LDA, Random Forest, and Neural Networks, each of which have different benefits and constraints. Generally, the main requirement of these algorithms are a sufficient number of samples to generate meaningful results.

Figure 5:
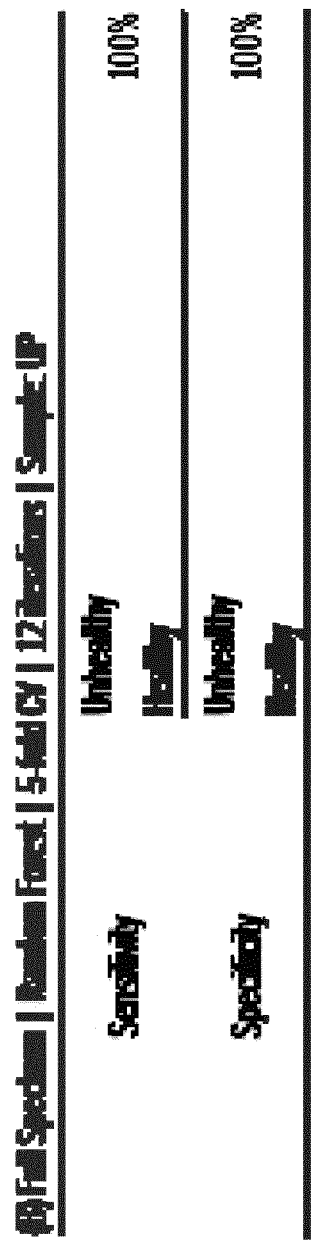
FIG. 5 shows results from a random forest classification for first a multi-class classifier of all cell classes (A), and binary classification based upon healthy and non-healthy (B)

In the examples presented here, the current dataset is limited as the data has been obtained from one sample vial, split into 9 technical replicates, of four treatment types. However, preliminary attempts have been made here to look into sample classification, It is possible to conduct a multi-class classifier on data with multiple comparators, however due to limited data, this is not immediately possible for this study. This can however be simplified to just healthy versus unhealthy cells/cell conditions, which is a simpler approach. The initial results show 100% sensitivity and specificity which is extremely promised. However, the results have been obtained from a small dataset that needs to be expanded in order to generate statistically significant results (see FIG. 5).

Figure 6:
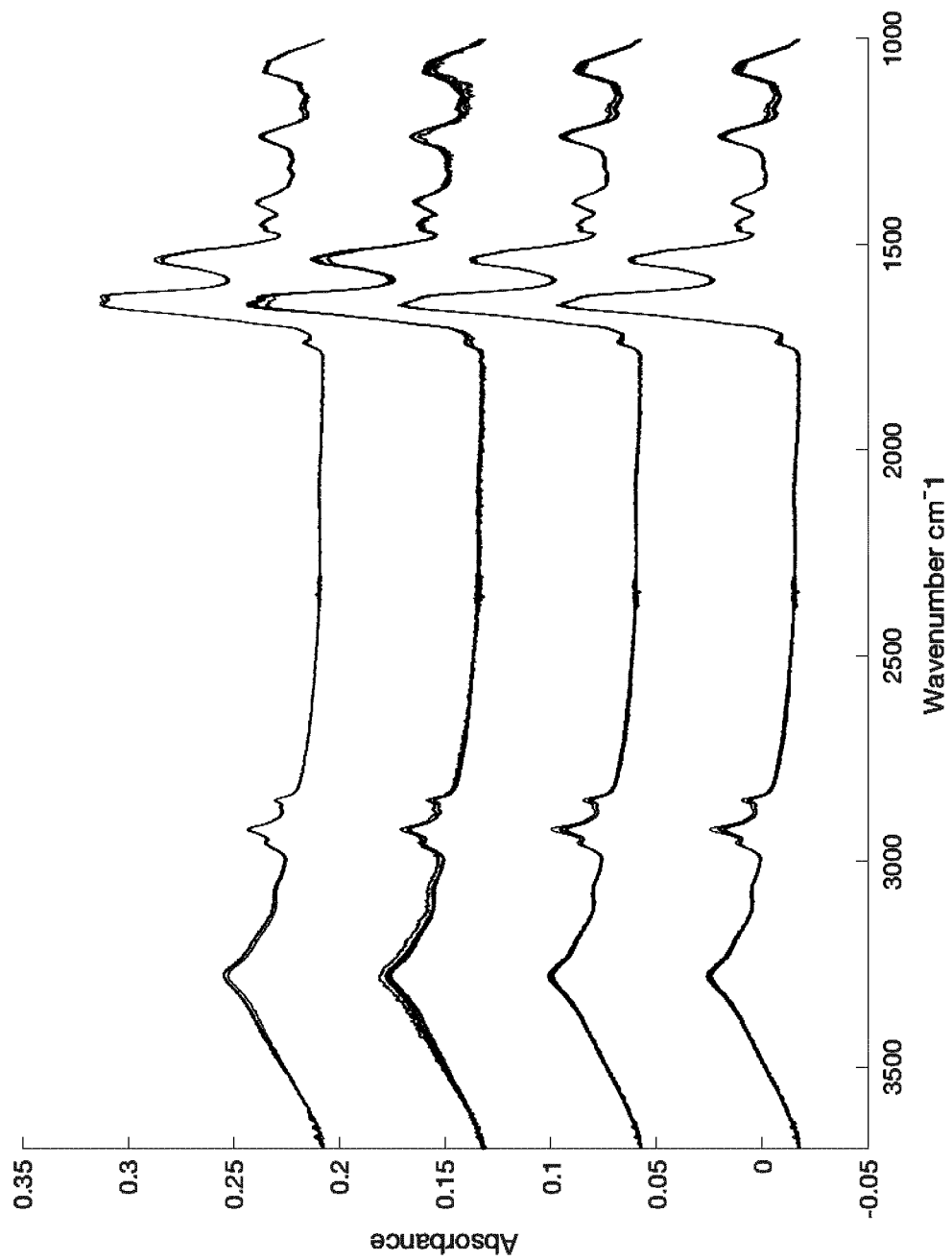
FIG. 6 shows the spectral analysis of dried CHO cells that have been fixed during sample preparation.
Figure 7:
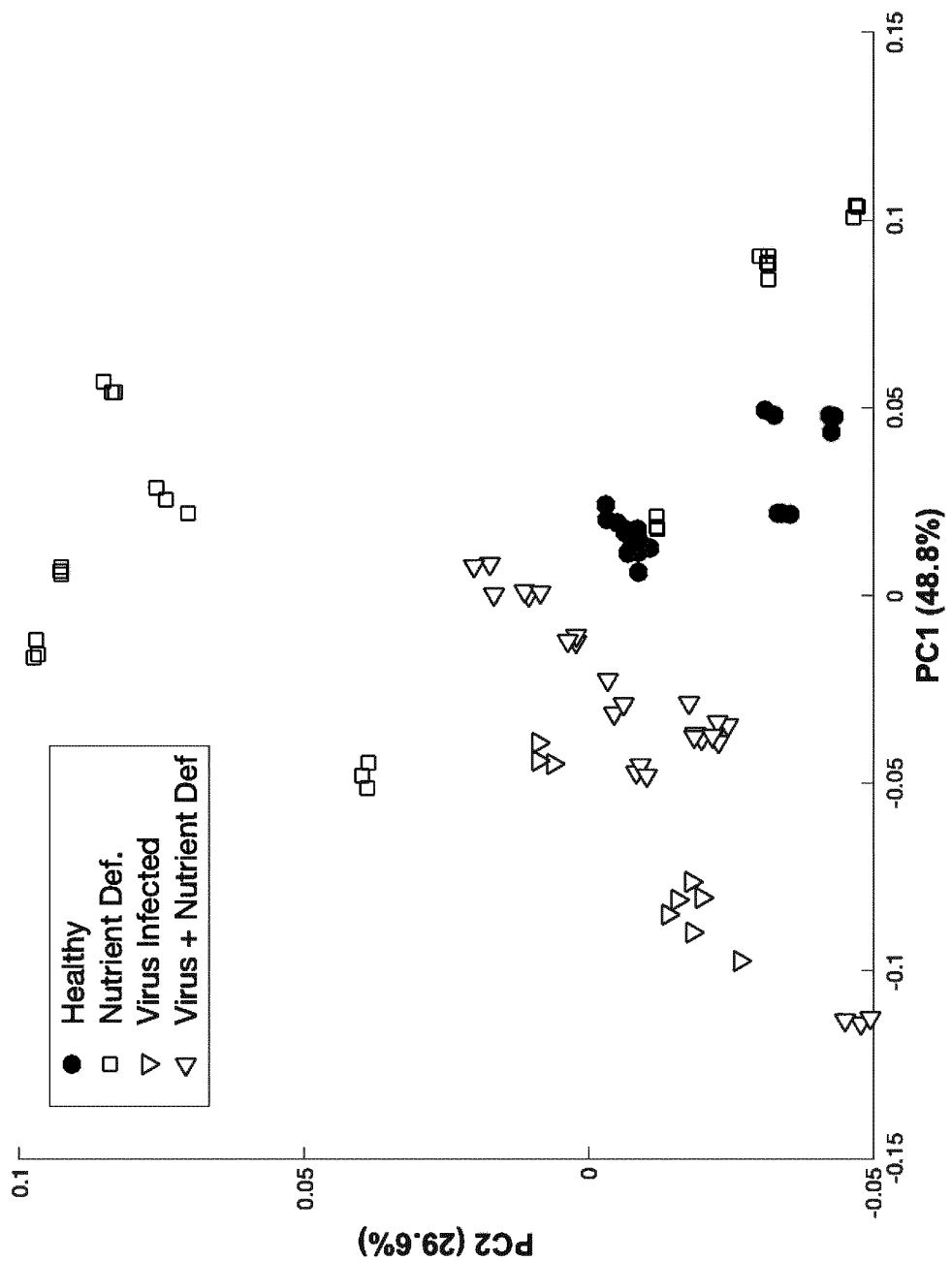
FIG. 7 shows PCA processed analysis of dried, fixed, CHO cells obtained from the spectral data displayed in FIG. 6.
Figure 8A:
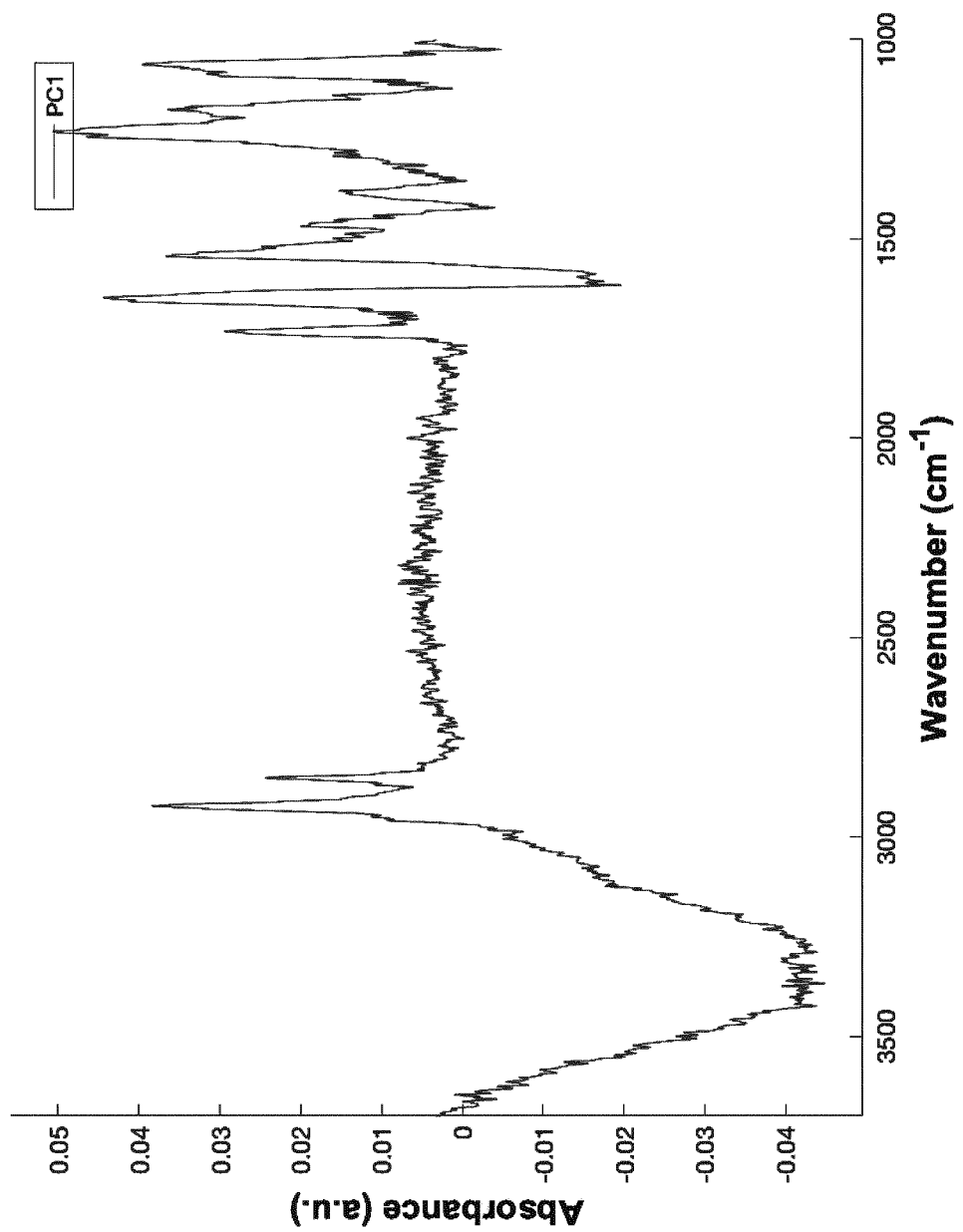
FIGS. 8a and 8b shows the spectral sources of variance in PC1 (A) and PC2 (B) across the spectrum between healthy and unhealthy cells, following fixation as an optional sample preparation step.
Figure 8B:
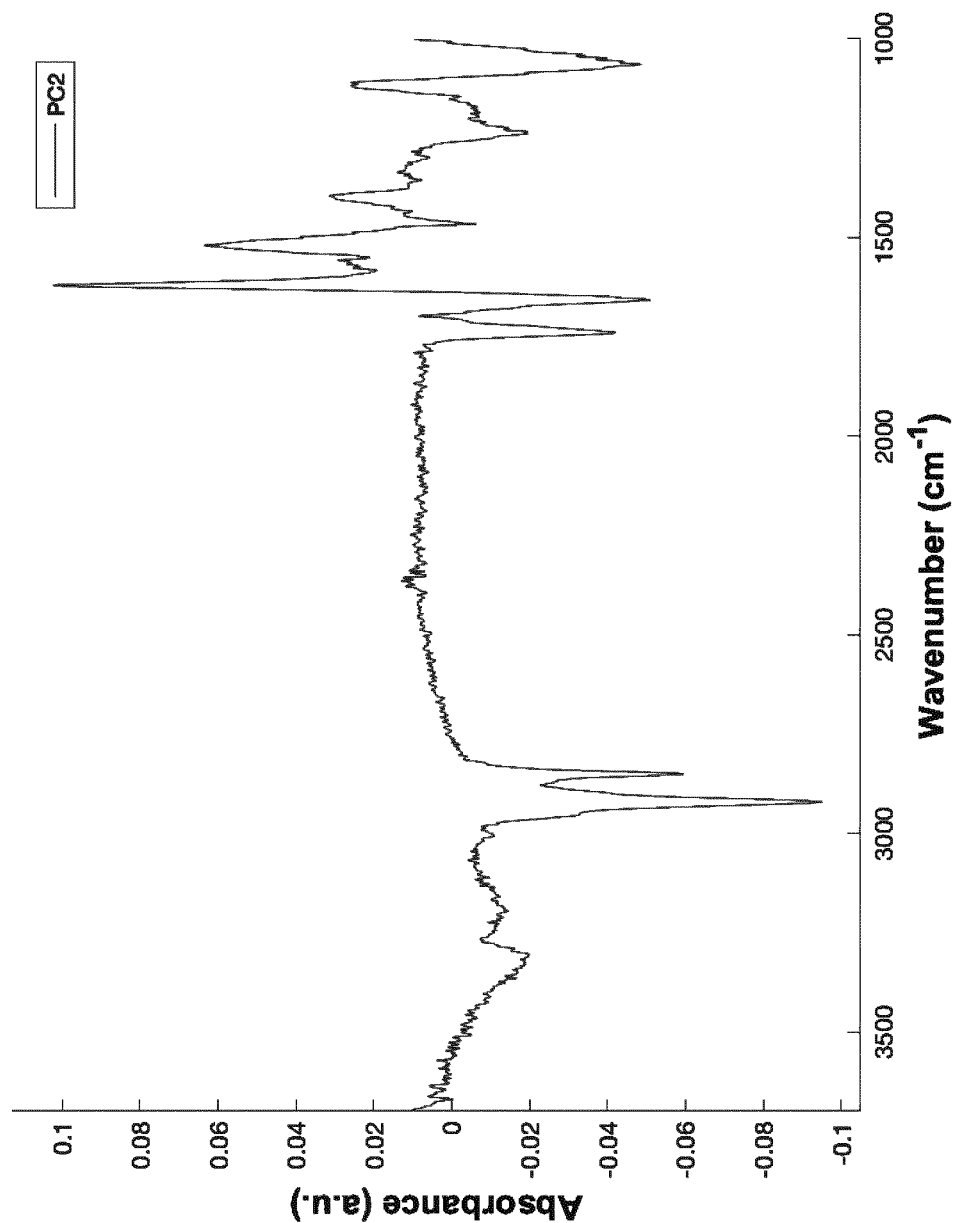

Similar patterns are observed with our other analyses too, with fixed cells showing subtle differences across the spectrum (FIG. 6). Fixation does appear to alter the biochemical composition of cells, which is largely seen in the lipid regions of the cells. However, this change is consistent between samples, and fixes them in their pre-frozen state so that the treatment response can be compared. PCA shows begins to highlight spectral differences more clearly. FIG. 7 displays variance between healthy and unhealthy cells, particularly with virally infected cells appearing more negative in PC1. Looking at the loading of PC1 (FIG. 8a), this is associated with widespread differences across the fingerprint region of the spectrum compared to healthy cells. Nutrient deficient cells appear predominantly more positive in PC2 (FIG. 7), which the relative loadings plot suggests is associated with lipid changes compared to healthy and virally infected cell lines. Without being bound by theory, this may be due to the fixation process.

Figure 9:
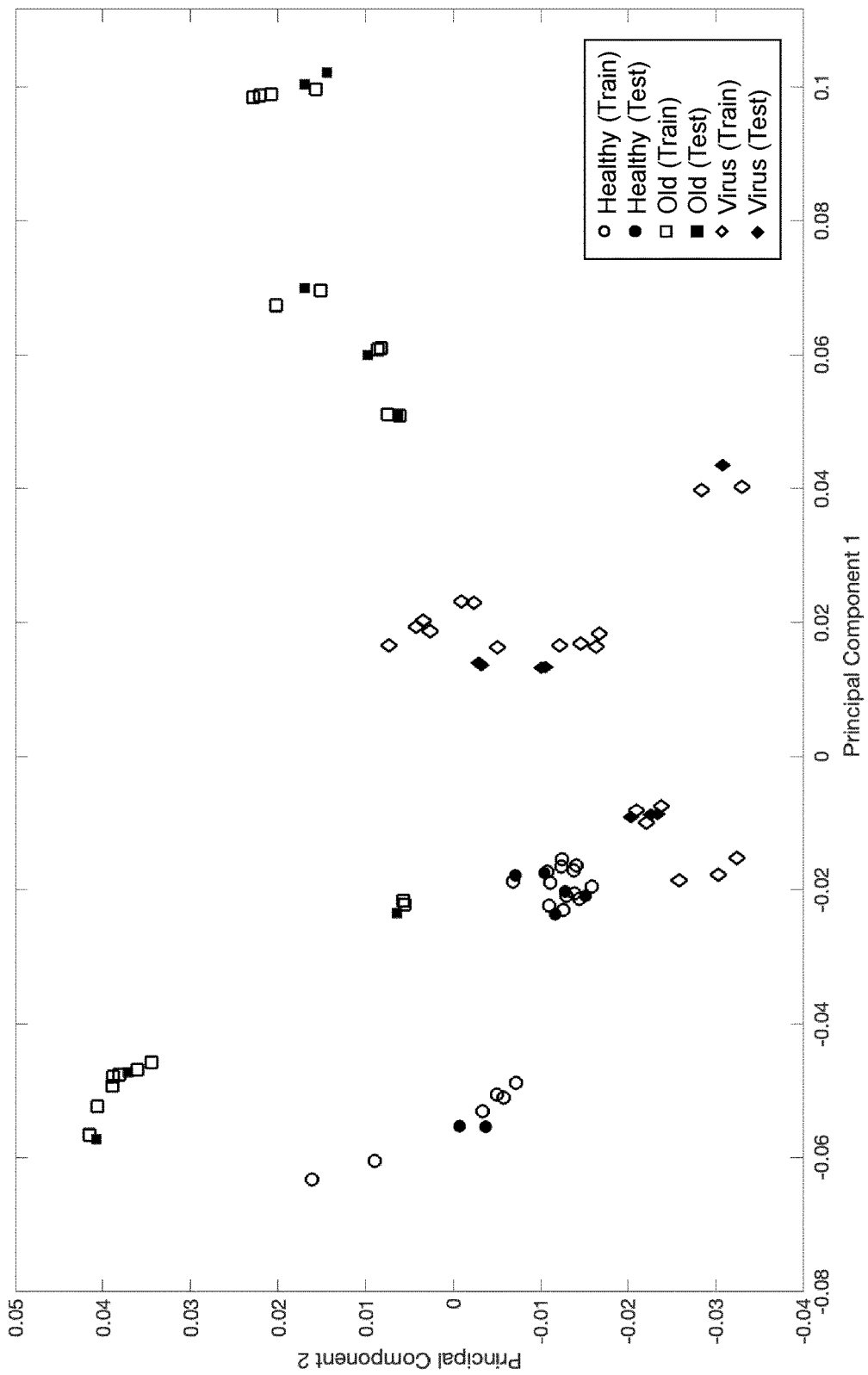
FIG. 9 shows projected PCA scatterplot analysis of healthy, virally infected and nutrient depleted cells following fixation.
Figure 10:
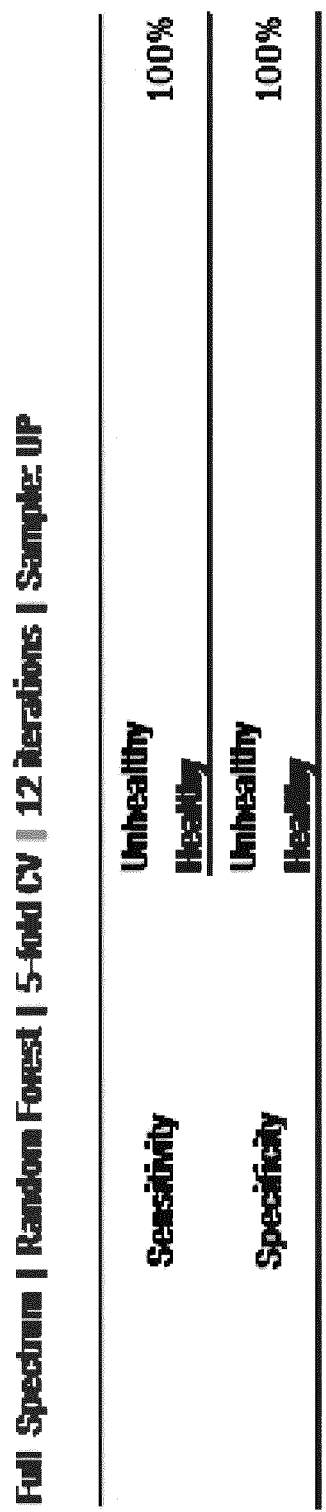
FIG. 10 shows the random forest binary classification results of the cells in FIG. 6, following fixation as a sample preparation step.

A full PCA projection is shown in FIG. 9 and interestingly good separation between the classes, particularly in PC1 and PC3 is observed. Again, the test projections highlighted as a box shadow, indicate that test sets work well. Classification was also relatively simple with regards to healthy versus unhealthy (see FIG. 10). Again, the caveat is that this is derived from a small dataset.

Figure 11:
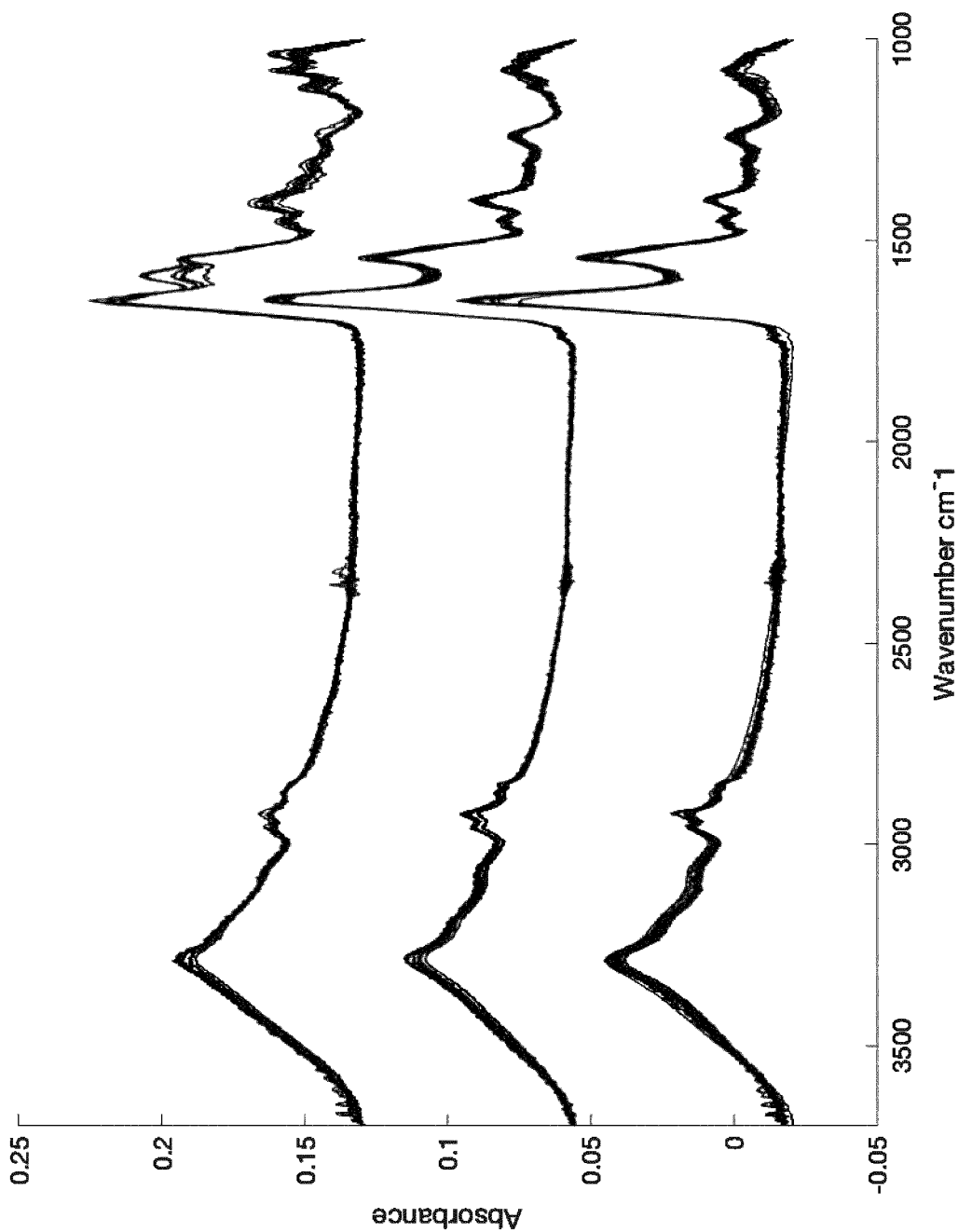
FIG. 11 shows processed spectra from supernatant material from healthy, virally infected and nutrient depleted cells.
Figure 12:
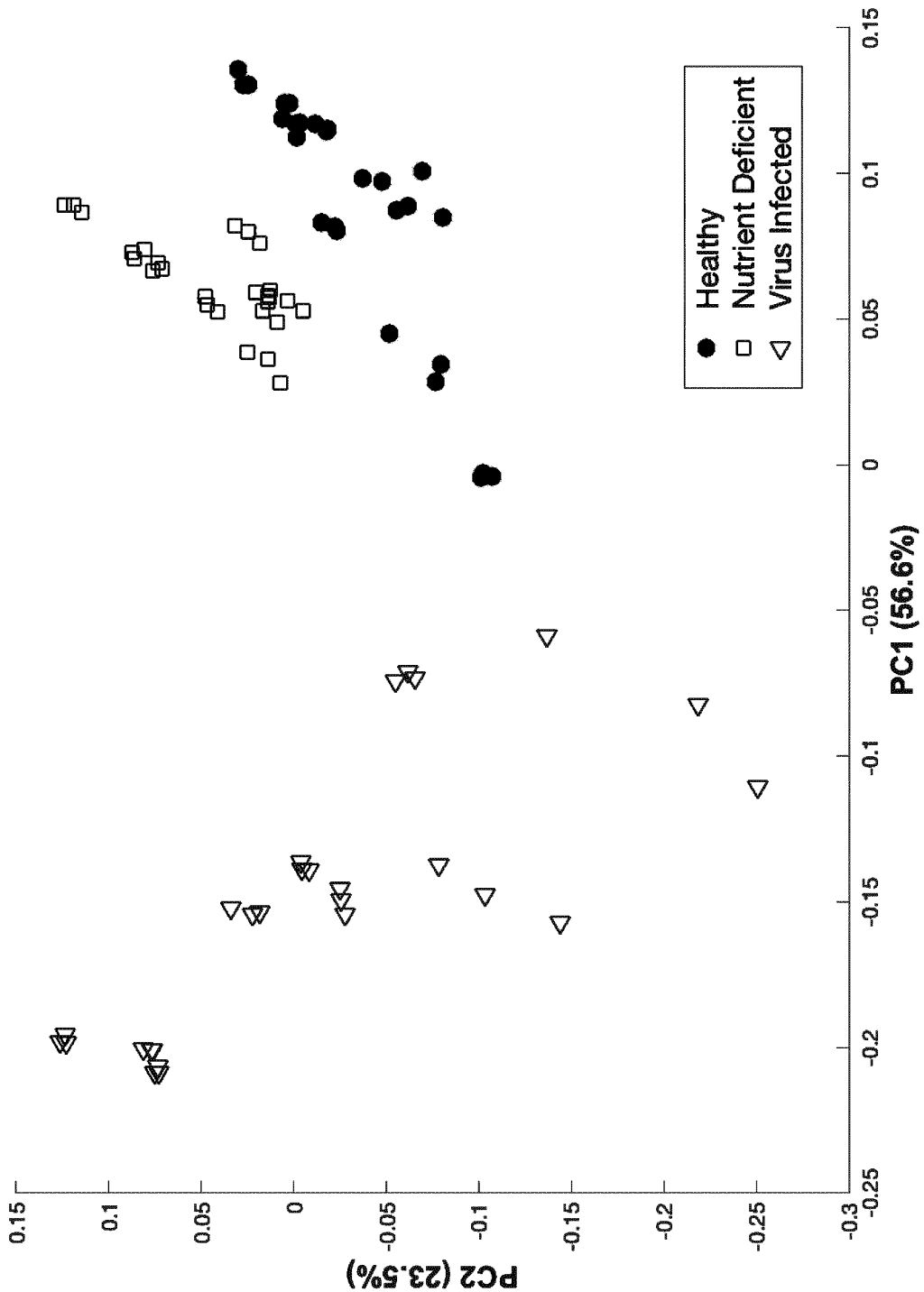
FIG. 12 shows PCA scatterplot analysis from supernatant material from healthy, virally infected and nutrient depleted cells.
Figure 13A:
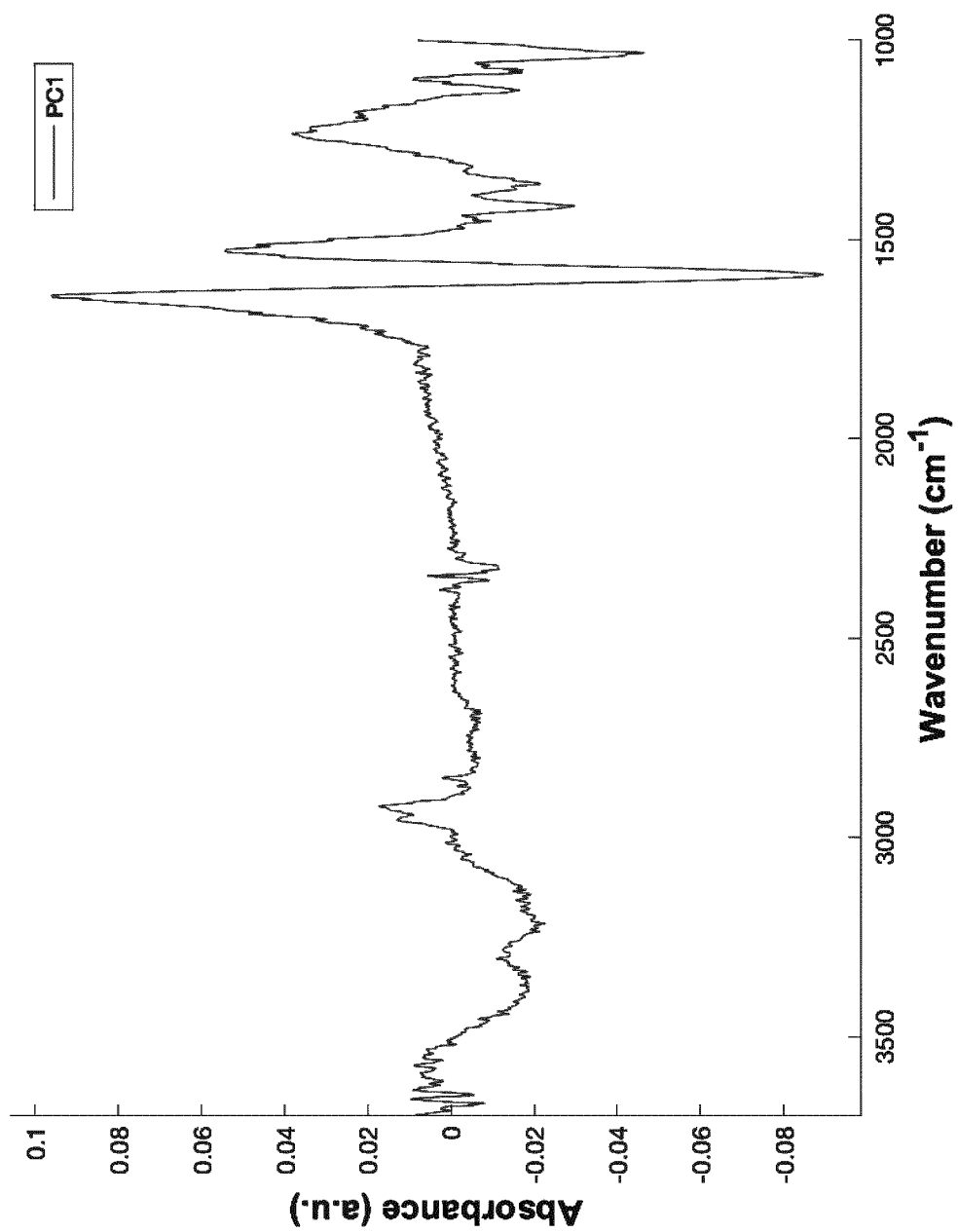
FIGS. 13a and 13b shows variance arising from PC1 (a) and PC2 (b) following PCA showing clear differences in the amide regions.
Figure 13B:
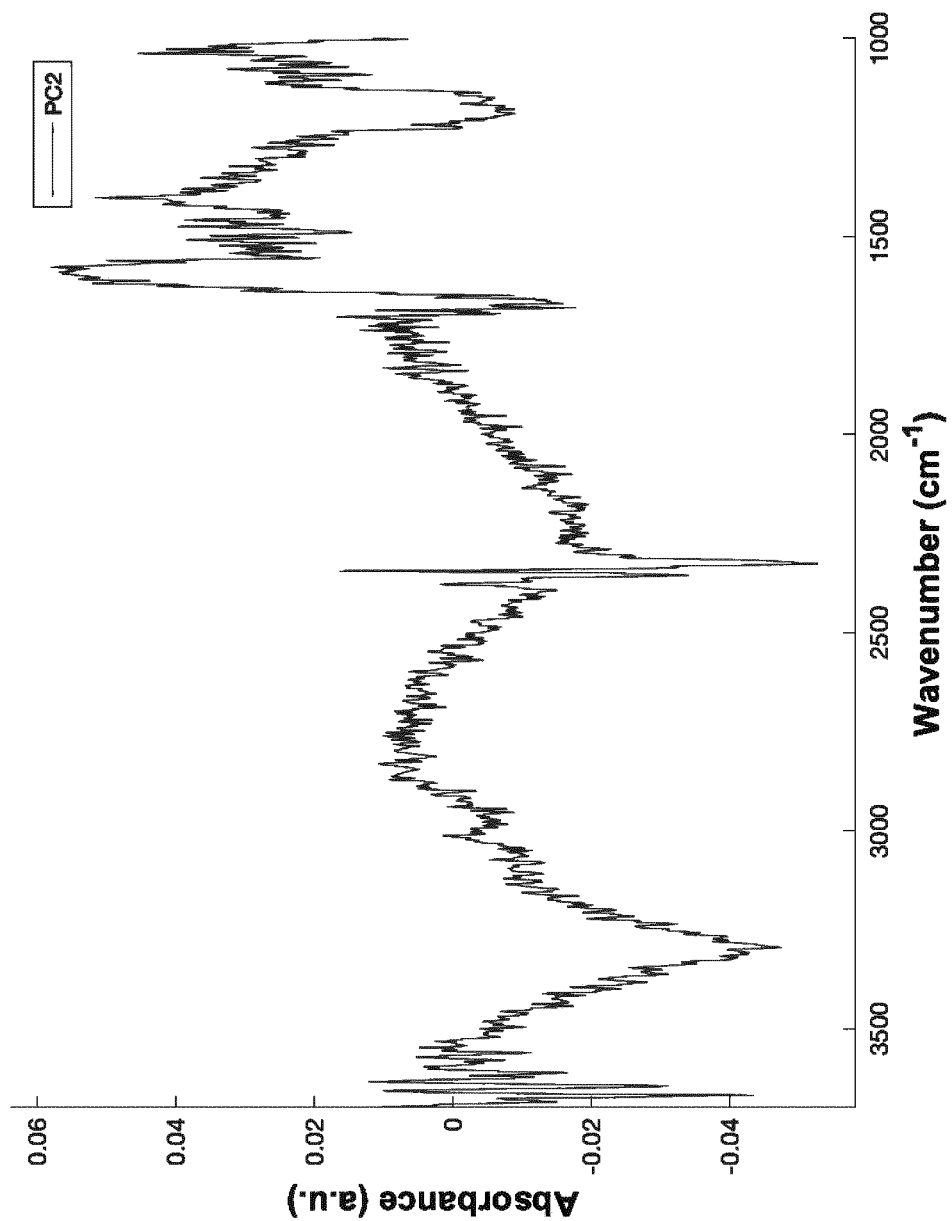

It is clear that both fixed and un-fixed cell samples can be used for the purpose of determining cell health, with some further studies in order to support these earlier investigations. As well as using samples of frozen cell samples, the inventors also studied cell supernatant. In FIG. 11, aspirated supernatant of a cell pellet containing cell media, fragments and related products, from the previous nutrient deficient and virally infected cell lines was analysed. Spectral differences can be seen immediately. Virally infected cells in particular display large spectral variances through the fingerprint region. Without wishing to be bound by theory, it is possible that some cellular material may be present in these samples to a varying degree. As shown in FIG. 12, these spectral differences contribute to good split in PC1 between virus infected cells, and also in PC2, discriminating nutrient deficient cells. PC1 is largely displaying amide I alterations because of infection (FIG. 13a), indicating protein differences, whereas PC2 describes more subtle variances across the spectrum (FIG. 13b).

Figure 14:
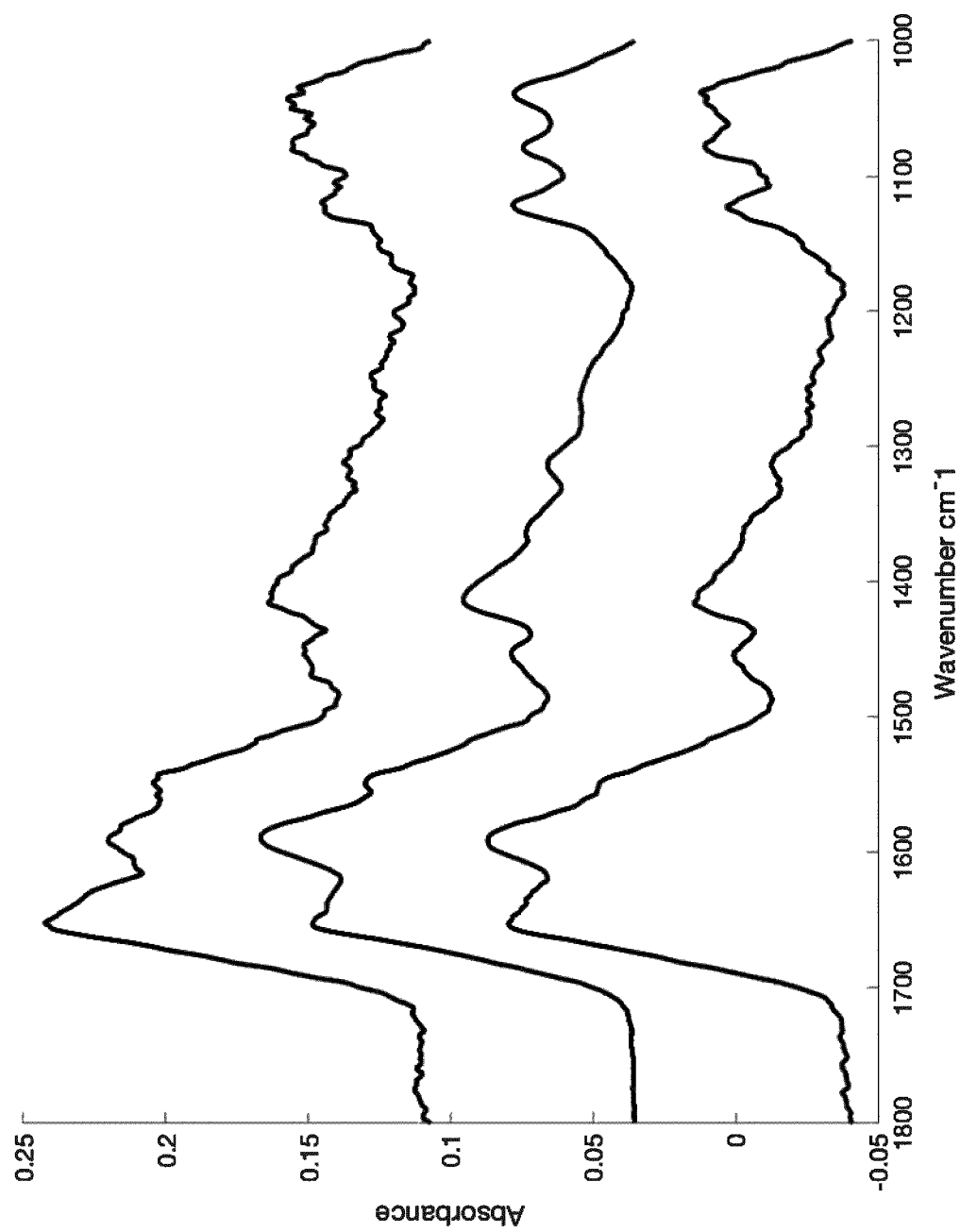
FIG. 14 shows processed spectra in the fingerprint region of supernatant samples derived from healthy and two types of virally infected CHO cells.
Figure 15:
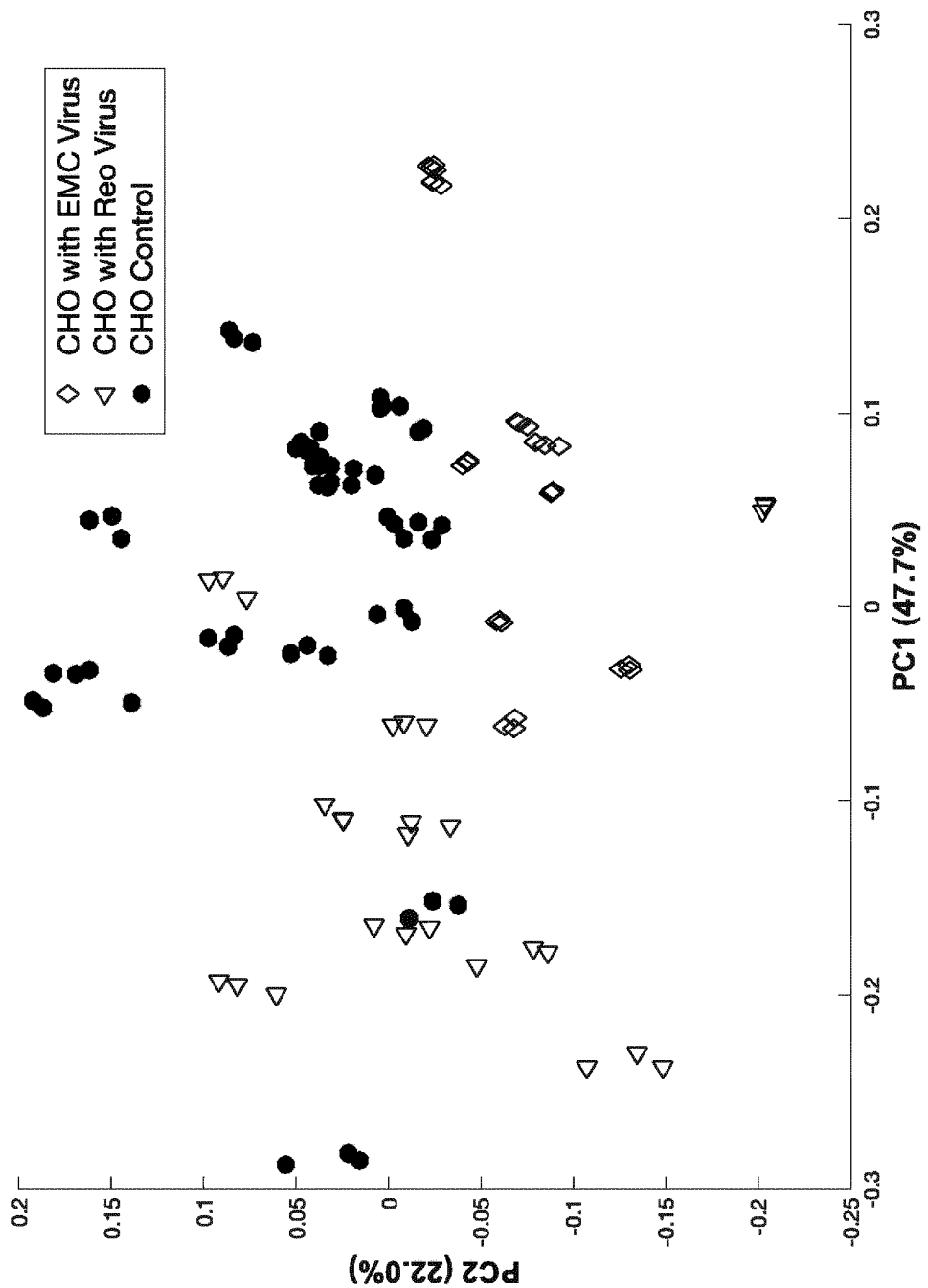
FIG. 15 shows PCA scatterplot analysis of processed spectra in the fingerprint region of supernatant samples derived from healthy and two types of virally infected CHO cells.

In another instance, supernatant was analysed in a separate virus focused study, investigating the impact of Reo virus, and also the EMC virus. Sample acquisition, preparation and analysis are the same as previously described. In FIG. 14, the raw spectra from healthy and virally infected cells are shown. The fingerprint region was focused upon as differences are more pronounced when focusing in this region, with a clear difference arising in the virus infected cells between the amide I and amide II peaks (see FIG. 14). Clear differences are evident between supernatants obtained from various cell culture conditions following PCA, particularly with EMC infection appearing more negatively in PC2 (FIG. 15).

The invention claimed is:

1. A method for detecting a status of cells within an in vitro cell culture, the method comprising:
   providing an Attenuated Total Reflection-Fourier Transform Infrared (ATR-FTIR) spectrum from a test sample obtained from a cell medium within the in vitro cell culture; and
   ii) comparing the ATR-FTIR spectrum with an ATR-FTIR spectrum of a control sample or samples, or a sample or samples obtained at an earlier time point of the cell medium within the in vitro cell culture to the test sample, in order to detect any difference between the test and control or earlier samples, which can be correlated with the status of cells within the test sample obtained from the cell medium within the in vitro cell culture, wherein the status of cells within the in vitro cell culture relates to the health of the cells, and wherein the ATR-FTIR spectra are collected at wavenumbers in the region of 400-4000 $cm^{-1}$.

2. The method of claim 1, wherein the sample or samples is obtained from the cell culture manually, by a semi-automated, or fully automated system associated with the cell culture.

3. The method of claim 1, the method being implemented and/or controlled by a computer system with integrated software in order to conduct the comparison step and detect any differences between the test sample and control or earlier samples obtained from the cell culture.

4. The method of claim 1, wherein the status of the cells is detected as being healthy, or unhealthy.

5. The method of claim 4, wherein the unhealthy status of the cells, is due to the cells being infected by a virus or bacteria, or due to the cells having developed an abnormality.

6. The method of claim 5, wherein the abnormality has occurred due to one or more cell culture conditions selected from the group consisting of a change in pH, oxygen levels, toxic component build up and nutrient levels.

7. The method of claim 1, wherein the cell culture comprises cells which produce a product, such as a recombinant protein or the like; or, the cells are the product.

8. The method of claim 7, wherein the cells are the product and are intended for in vivo and/or in vitro application.

9. The method of claim 1, wherein the cells are bacterial or eukaryotic cell types.

10. The method of claim 1, wherein the test sample or control sample is a wet sample or a dry sample, which has been obtained directly or indirectly from the cell culture.

11. The method of claim 1, wherein the step of comparing the ATR-FTIR spectra is performed using a predictive model.

12. A computer-implemented method of correlating the results of an Attenuated Total Reflection-Fourier Transform Infrared (ATR-FTIR) spectroscopic analysis method of a test sample obtained from a cell medium within an in vitro cell culture, with a status of cells related to health within the bi vitro cell culture, the method comprising:
   collecting data from said spectroscopic analysis; and
   employing a predictive model, suitably based on pattern recognition algorithms conducted upon pre-correlated spectroscopic analyses to correlate said data with the status of cells within the cell culture.

13. An integrated cell culture and infrared analysis system comprising:
   a) an in vitro cell culture apparatus for growing cells in culture;

b) an Attenuated Total Reflection-Fourier Transform Infrared (ATR-FTIR) spectrometer;
c) a sample handling system for obtaining one or more cell samples from a cell medium within a cell culture within the in vitro cell culture apparatus, the sample handling system comprising a sampler for obtaining a sample from the cell medium within the cell culture and transporting the one or more cell samples to the ATR-FTIR spectrometer in order that an ATR-FTIR spectrum of the sample or samples may be obtained at wavenumbers in the region of 400-4000 $cm^{-1}$; wherein the system is configured to conduct a method to detect a status of cells related to health within the cell culture.

14. The system according to claim 13, wherein the integrated system further comprises an ability to, i) alert a user, ii) alter the cell culturing process; and iii) halt the cell culturing process.

* * * * *